United States Patent
Christensen et al.

(10) Patent No.: US 11,383,041 B2
(45) Date of Patent: Jul. 12, 2022

(54) PREFILLED INJECTION DEVICE WITH CLEANING CHAMBER

(71) Applicant: Novo Nordisk A/S, Bagsvaerd (DK)

(72) Inventors: Martin Johst Christensen, Copenhagen (DK); Bjoern Gullak Larsen, Birkeroed (DK); Kurt Solgaard, Graested (DK); Carsten Soerensen, Frederiksberg (DK)

(73) Assignee: Novo Nordisk A/S, Bagsvaerd (DK)

( * ) Notice: Subject to any disclaimer, the term of this patent is extended or adjusted under 35 U.S.C. 154(b) by 413 days.

(21) Appl. No.: 16/480,487

(22) PCT Filed: Jan. 19, 2018

(86) PCT No.: PCT/EP2018/051338
§ 371 (c)(1),
(2) Date: Jul. 24, 2019

(87) PCT Pub. No.: WO2018/138016
PCT Pub. Date: Aug. 2, 2018

(65) Prior Publication Data
US 2020/0001015 A1 Jan. 2, 2020

(30) Foreign Application Priority Data
Jan. 25, 2017 (EP) .................................... 17152991

(51) Int. Cl.
*A61M 5/315* (2006.01)
*A61M 5/20* (2006.01)

(52) U.S. Cl.
CPC .......... *A61M 5/31528* (2013.01); *A61M 5/20* (2013.01); *A61M 5/31568* (2013.01);
(Continued)

(58) Field of Classification Search
CPC ................ A61M 5/31528; A61M 5/20; A61M 5/31568; A61M 5/31541; A61M 5/315553; A61M 5/31533; A61M 5/31565
See application file for complete search history.

(56) References Cited

U.S. PATENT DOCUMENTS

RE41,956 E 11/2010 Klitgaard et al.
8,920,383 B2 12/2014 Enggaard et al.
(Continued)

FOREIGN PATENT DOCUMENTS

CN 104736188 A 6/2015
EP 1351732 1/2001
(Continued)

*Primary Examiner* — Nathan R Price
*Assistant Examiner* — Tasnim Mehjabin Ahmed
(74) *Attorney, Agent, or Firm* — Wesley Nicolas

(57) ABSTRACT

The invention relates to an injection device comprising an End-of-Content mechanism. The End-of-Content mechanism comprises a piston rod (10) being driven forward by a rotatable piston rod guide (20), a driver (50) attached to a dose setting tube (30) and an End-of-Content tube (40). The End-of-Content tube is moved axially forward during dose setting a distance which correlates to the size of the dose being set. When the accumulated set and ejected dose equals the injectable amount initially available in the cartridge (3), the End-of-Content tube engages a lock mechanism provided in the piston rod guide and the driver engages a stop surface on the End-of-Content tube. Once the End-of-Content mechanism is locked, no further dose can be set and the piston rod guide cannot be rotated. In order to provide a proper engagement between the piston rod guide and the driver, the End-of-Content mechanism is released during dose expelling.

11 Claims, 5 Drawing Sheets

(52) U.S. Cl.
CPC ..... *A61M 5/31533* (2013.01); *A61M 5/31541* (2013.01); *A61M 5/31553* (2013.01); *A61M 5/31565* (2013.01)

(56) References Cited

U.S. PATENT DOCUMENTS

| | | |
|---|---|---|
| 9,114,211 B2 | 8/2015 | Enggaard et al. |
| 9,492,619 B2 | 11/2016 | Raab |
| 9,861,755 B2 | 1/2018 | Beek et al. |
| 2002/0120235 A1 | 8/2002 | Enggaard |
| 2012/0245532 A1 | 9/2012 | Frantz et al. |
| 2013/0123685 A1 | 5/2013 | Jespersen et al. |
| 2015/0174335 A1 | 6/2015 | Roervig et al. |

FOREIGN PATENT DOCUMENTS

| | | | | |
|---|---|---|---|---|
| JP | 2004516895 A | 6/2004 | | |
| JP | 2015521511 A | 7/2015 | | |
| WO | 02053214 A1 | 7/2002 | | |
| WO | 2006/128794 | 12/2006 | | |
| WO | 2016001307 A1 | 1/2016 | | |
| WO | WO-2016001307 A1 * | 1/2016 | ........ | A61M 5/31553 |
| WO | 2016180873 A1 | 11/2016 | | |

* cited by examiner

PREFILLED INJECTION DEVICE WITH CLEANING CHAMBER

CROSS-REFERENCE TO RELATED APPLICATIONS

This application is a 35 U.S.C. § 371 National Stage application of International Application PCT/EP2018/051338 (published as WO 2018/138016), filed Jan. 19, 2018, which claims priority to European Patent Application 17152991.0, filed Jan. 25, 2017, the contents of all above-named applications are incorporated herein by reference.

THE TECHNICAL FIELD OF THE INVENTION

The invention relates to a medical injection device for injecting a liquid drug and especially to a pre-filled injection device for apportioning a multiple number of individual settable doses. The invention further relates to such pen-shaped and pre-filled injection device wherein the injection device comprises an End-of-Content mechanism.

DESCRIPTION OF RELATED ART

An injection device with a mechanical End-of-Content mechanism is disclosed in U.S. RE41,956. The drive element driving the piston rod forward is provided with a track having a length that correlates to the total injectable content of liquid drug contained in the injection device. A follower which is guided in this track is coupled to the dose setting mechanism such that each time a user sets a specific dose, the follower is moved a certain distance relating to the size of the set dose in the track. When the user expels the set dose, the follower is maintained in its relative position in the track. The position of the follower in the track is thus an indicator for how much liquid drug has been set and ejected. Once the follower reaches the end of the track, the dose setting mechanism is blocked such that a further dose cannot be set. It is thereby secured that the end of the track is reached once the accumulated doses a user has set and ejected equals the total injectable content contain in the injection device.

A similar End-of-Content mechanism is disclosed in U.S. Pat. No. 9,114,211. In this EoC mechanism, the track is provided on an inner surface of the housing and the follower is moved in the track every time the user rotates the dose setting member. Once the follower physically reaches the end of the track the dose setting member cannot be rotated further.

In some spring operated injection devices, the dose to be ejected is released by axial movement of a needle shield. Such shield triggering of the dose release often requires axially movable parts in the injection mechanism and many of the known End-of-Content systems are not able to operate together with axially movable parts.

DESCRIPTION OF THE INVENTION

It is an object of the present invention to provide an injection device having axially movable parts for releasing the set dose without these parts obstructing the End-of-Content mechanism.

Accordingly, in a general aspect of the present invention a prefilled injection pen for apportioning multiple set doses of a liquid drug comprises:

A housing which in one example includes a cartridge holder for securing a cartridge containing the liquid drug to be ejected.

A rotatable piston rod which is moved forward inside the cartridge to thereby drive out the set doses from the cartridge. The piston rod has an outer thread and a longitudinal non-threaded area e.g. in the form of a longitudinal groove or the like.

A piston rod guide which is rotatable during dose expelling only, by the word "only" is meant that the piston rod guide only rotates during dose expelling but is kept inrotatable during dose setting. The piston rod guide further engages the longitudinal non-threaded area of the piston rod to thereby translate rotation of the piston rod guide to rotation of the piston rod.

A rotatable drive element for rotating the piston rod guide during dose expelling. The drive element is axially movable between a first setting position and a second dose expelling position;

in the first dose setting position, the drive element is disengaged from the piston rod guide, and in the second dose expelling position, the drive element is engaged with the piston rod guide.

A torsion spring encompassed between the housing or at least a part fixed to the housing and the drive element. The torsion spring holds a torque for rotating the drive element during dose expelling, An End-of-Content (EoC) tube having an inwardly pointing ridge engaging the non-threaded area of the piston rod to thereby rotate with the piston rod during dose expelling. Consequently the EoC tube is prevented from rotation by the engagement with the piston rod when the piston rod is not rotated. On the outer surface, the EoC tube is provided with a helical thread.

A rotatable dose setting tube coupled to the drive element and provided with a thread segment threadely engaging the outer thread of the EoC tube.

During dose setting; rotation of the dose setting tube and the drive element relatively to the piston rod which do not rotate during dose setting causes the EoC tube to move distally an axial distance in relation to the dose setting tube due to the threaded engagement between the rotatable dose setting tube and the EoC tube engaging the piston rod; the axial distance correlating to the size of the set dose and the EoC tube being able to move distally until a proximal stop surface provided on the EoC tube (engages the thread segment on the dose setting tube thereby preventing further distal movement of the EoC tube and further rotation of the rotatable dose setting tube.

During dose expelling; the dose setting tube, the drive element, the piston rod guide and the EoC tube rotate together which maintains the EoC tube in its relative position in relation to the dose setting tube.

Consequently whenever a dose is set, the EoC tube is moved distally an axial distance corresponding to the set dose. The length the EoC tube is able to move distally is thus an expression of the injectable content contained in the cartridge such that whenever the EoC tube enters into its locked position no further doses can be set. It is henceforth secured that the user can not set a dose which exceeds the injectable content remaining inside the cartridge at any time. The locked position is established by an engagement between the thread segment provided on the dose setting tube and a stop surface provided on the EoC tube. Every time a dose is set by the user, the EoC tube and the stop surface is moved towards the thread segment provided on the dose setting tube and the length the EoC tube can move is henceforth an expression of the injectable content of the cartridge. Since the dose setting tube rotates relatively to the EoC tube during dose setting, the movable length is actually the length of the outer thread provided on the EoC tube and once the stop surface reaches and engages the thread segment no further doses can be set.

The set dose is expelled by an axial movement of the drive element which is axially movable between the first dose setting position and the second dose expelling position.

Since the dose setting tube is coupled to the drive element, these two element moves in unison in all movements. The coupling between the drive element and the dose setting tube is such that the two elements both move axially and rotatable together. In one example the two parts can be moulded as one single element.

The drive element is preferably moved from the first dose setting position to the second dose expelling mechanism by an axially movable needle shield which is pushed against the skin of the user during injection. In the disclosed embodiment an axially movable release element transforms the axial movement of the needle shield to the axial movement of the drive element.

Further, the proximal movement of the drive element and the dose setting tube causes the EoC tube to also move proximally. As the EoC tube moves proximally it moves out of engagement with the piston rod guide. The piston rod guide is thus free to rotate a few rotational degrees during dose expelling which makes the engagement with the drive mechanism easier.

In one example the thread segment provided on the dose setting tube is provided on an inner surface thereof.

The piston rod guide is preferably provided with an inwardly pointing knob for engaging the longitudinal non-threaded area of the piston rod. In one example, the non-threaded area is a longitudinal groove into which the inwardly pointing knob fits to form a nut and groove engagement.

In a further example, the EoC tube is provided with distal stop surfaces which in the stop position engages the inwardly pointing knob on the piston rod guide such that the rotational torque occurring when the user try to rotate the dose setting tube (by rotating the dose setting button) is obtained by the piston rod guide. Otherwise the user could break the stop engagement between the EoC tube and the dose setting tube.

Proximally the EoC tube carries a proximal stop surface which at the End-of-Content engages with the thread segment provided internally in the dose setting tube. This proximal stop surface prevent the user form rotating the dose setting tube further once the proximal stop surface engages the thread segment provided internally in the dose setting tube. In one example the proximal stop surface form part of the thread provided externally on the EoC tube.

Although the stop surface is described in singularity it can easily be divided into any random number of stop surfaces.

In order to prevent the piston rod guide and thus the piston rod from rotating in the direction moving the piston rod proximally a one-way toothing is provided on the piston rod guide which one-way toothing engages the housing or at least a housing component. It is thus secured that the piston rod guide and the piston rod can only move in one rotational direction.

During rotation the piston rod is screwed helically in the distal direction by having the outer thread on the piston rod engage a similar inner thread provided in the housing or in a housing component.

The piston rod guide is further provided with radial teeth for engaging the driver during dose expelling.

All though the thread provided on the inner surface of the dose setting tube is referred to as a thread segment such segment can have any length including a helical length longer than one full rotation.

Definitions

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

The term "Needle Cannula" is used to describe the actual conduit performing the penetration of the skin during injection. A needle cannula is usually made from a metallic material such as e.g. stainless steel and preferably connected to a needle hub to form a complete injection needle, all though the needle cannula could also be connected directly to the housing structure without a needle hub. A needle cannula could however also be made from a polymeric material or a glass material.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Cartridge" is the term used to describe the container actually containing the drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. Such septum is usually self-sealing which means that the opening created during penetration seals automatically by the inherent resiliency once the needle cannula is removed from the septum. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

Since a cartridge usually has a narrower distal neck portion into which the plunger cannot be moved not all of the liquid drug contained inside the cartridge can actually be expelled. The term "initial quantum" or "substantially used" therefore refers to the injectable content contained in the cartridge and thus not necessarily to the entire content.

An "End-of-Content" mechanism is a—mechanical or electronic—counter that counts and accumulates how much liquid drug has been set and ejected. Every time the user sets a new dose this is accumulated to the previously set and ejected doses and once the total accumulated amount of set and ejected doses reaches a predetermined level, the mechanism prevents the user from setting further doses. The predetermined level is usually the total amount that can be ejected from the particular injection device. If the injection device e.g. is the pre-filled injection device currently sold by Novo Nordisk A/S under the trade mark name FlexPen® or FlexTouch® which usually contains 3 millilitre of insulin or GLP-1, the End-of-Content mechanism continuously during dose setting counts and remembers the accumulated doses set and ejected, and once the total accumulated sum of the doses set and ejected reaches the 3 millilitres, the mechanism prevents the user from setting further doses.

By the term "Pre-filled" injection device is meant an injection device in which the cartridge containing the liquid drug is permanently embedded in the injection device such that it cannot be removed without permanent destruction of the injection device. Once the pre-filled amount of liquid drug in the cartridge is used, the user normally discards the entire injection device. This is in opposition to a "Durable" injection device in which the user can himself change the cartridge containing the liquid drug whenever it is empty. Pre-filled injection devices are usually sold in packages containing more than one injection device whereas durable injection devices are usually sold one at a time. When using pre-filled injection devices an average user might require as many as 50 to 100 injection devices per year whereas when using durable injection devices one single injection device could last for several years, however, the average user would require 50 to 100 new cartridges per year.

The term "Permanently connected" as used in this description is intended to mean that the parts, which in this application is embodied as a cartridge and a housing assembly, requires the use of tools in order to be separated and should the parts be separated it would permanently damage at least one of the parts.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

Detailed Description of Embodiment

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the injection device which usually carries the injection needle whereas the term "proximal end" is meant to refer to the opposite end pointing away from the injection needle and usually carrying the dose dial button.

Figure 1:
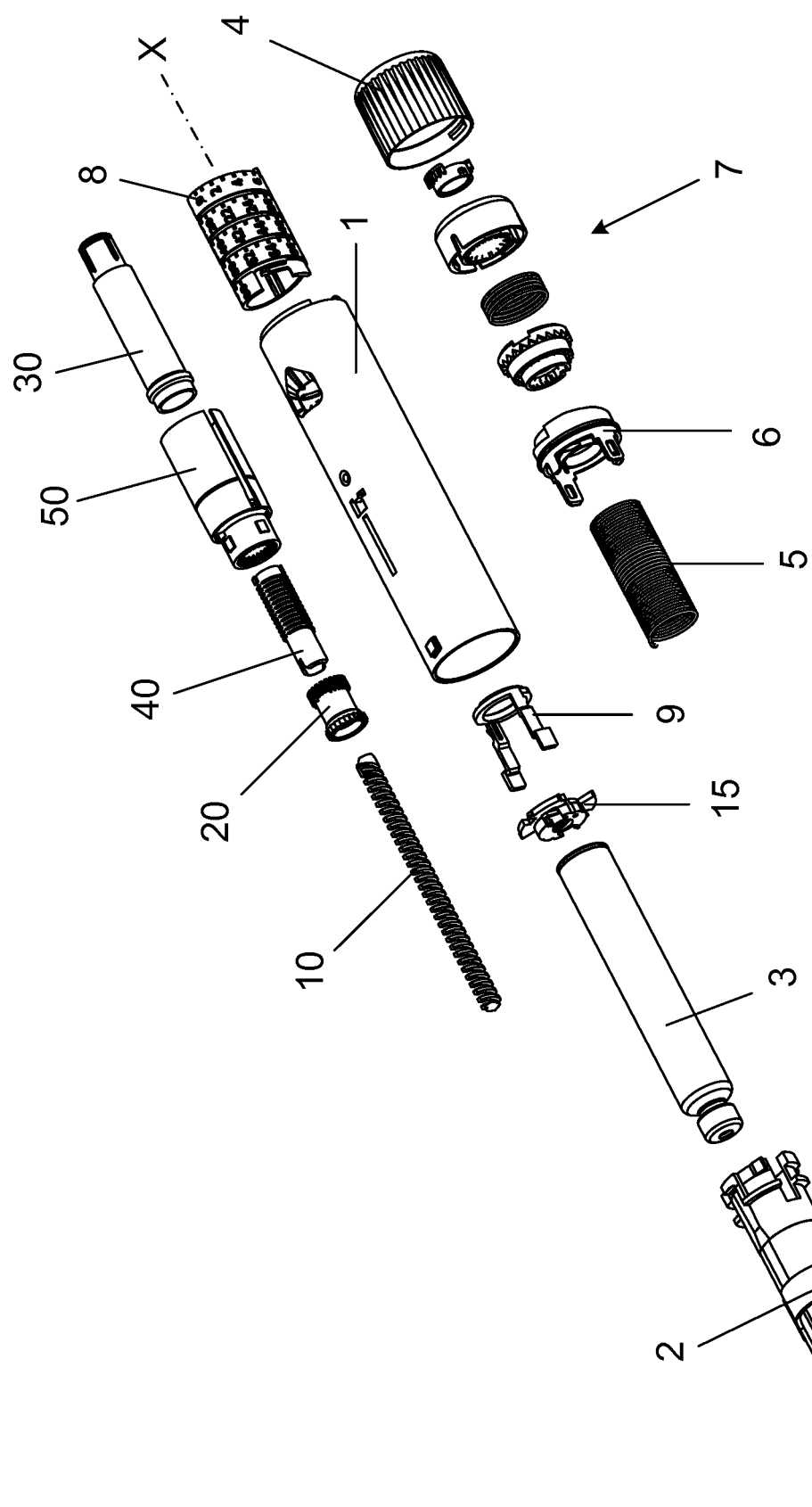
FIG. 1 show an exploded view of the injection device according to the invention.
Figure 2:
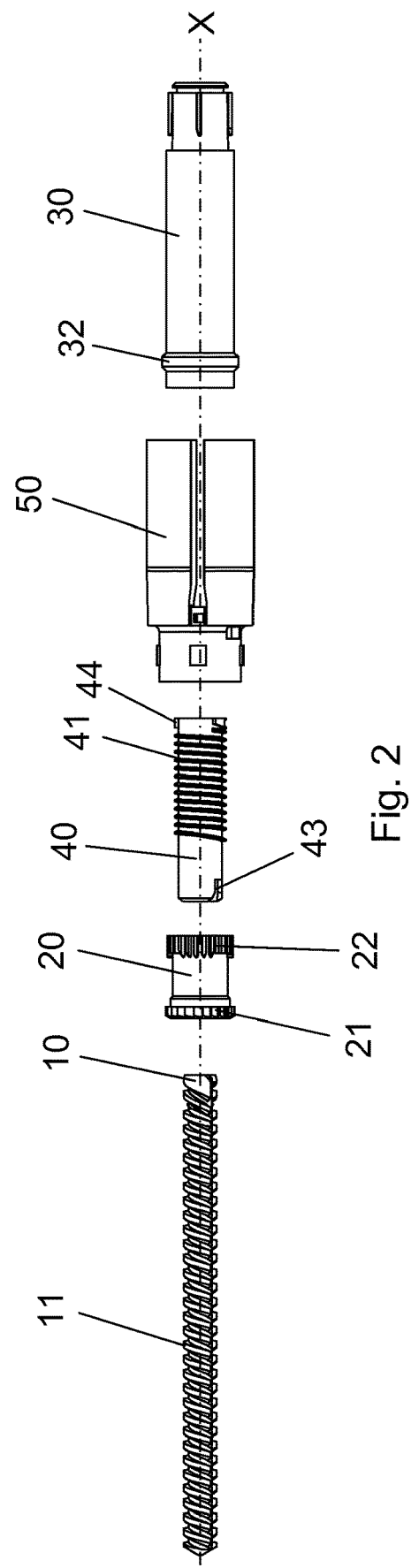
FIG. 2 show a side view of the End-of-Content (EoC) mechanism of the injection device depicted in FIG. 1.

Distal and proximal are meant to be along an axial orientation extending along the longitudinal axis "X" of the injection device as further indicated in FIGS. 1 and 2 where FIG. 1 discloses the motor part of the injection device.

Only the central elements of the End-of-Content mechanism of the injection device according to the present invention and as disclosed in FIG. 2 will be explained in details.

The motor part of the injection device is encapsulated in a housing 1 as disclosed in FIG. 1. The housing 1 is connected to a cartridge holder 2 securing the cartridge 3 containing the liquid drug to be injected.

Proximally a dose setting button 4 is provided which is rotational secured to the housing 1. A non-shown plunger is provided inside the cartridge 3 and a piston rod 10 is provided to move the plunger in the distal direction during dose expelling. The piston rod 10 is threaded to a nut member 15 which is secured in the housing 1 such that the piston rod 10 is moved helically forward when rotated as it is customary in these types of injection devices.

A not-shown injection needle is connected to the cartridge holder 2 such that the liquid drug can be delivered to a user through the lumen of such injection needle.

The dose expelling is executed by a torsion spring 5 which is strained during setting of the dose. The torsion spring 5 is encompassed between the housing 1 and the driver 50. The torsion spring 5 is in the disclosed exampled secured to the housing 1 via a spring base 6.

Between the spring base 6 and the dose setting button 4, a ratchet mechanism 7 is provided which secures the torque in the torsion spring 5 during rotation of the dose setting button 4. Further, a scale drum 8 is provided in order to display the size of the dose being set by rotation of the dose setting button 4. The scale drum 8 and the driver 50 are provided with a nut and groove connection such that the scale drum 8 rotates together with the driver 50. The scale drum 8 is preferably threaded to the housing 1 such that the scale drum 8 demonstrates a helical movement during its rotation.

The injection device disclosed is a so-called shield triggered injection device i.e. an injection device wherein the set dose is released by actuation of an axially movable shield.

In one example the axially movable shield can carry a cleaning chamber cleaning the distal tip of the injection needle between subsequent injections.

In the disclosed example, the axially movable shield is not depicted, but the shield surrounds the cartridge holder 2 and is moved in the proximal direction during dose expelling. A compression spring can be provided to return the axially movable shield once the injection has been performed. As the non-shown shield moves proximally it activates a release element 9 to also move proximally. This proximal movement of the release element 9 further moves the driver 50 in the proximal direction as will be explained.

Figure 5:
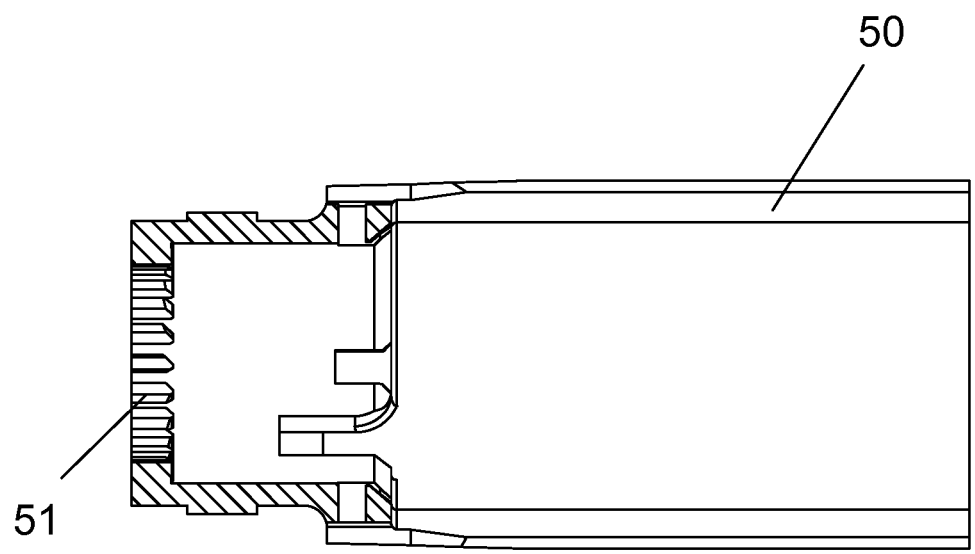
FIG. 5 show a side view of the driver.
Figure 6:
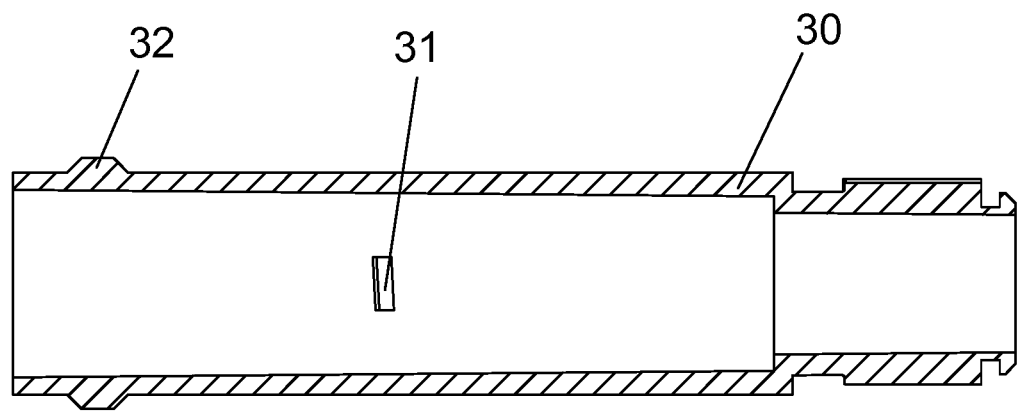
FIG. 6 show a side view of the dose setting tube.
Figure 7:
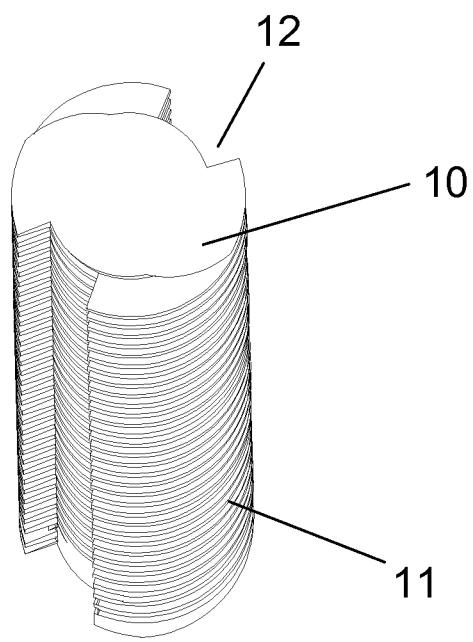
FIG. 7 show a perspective of the piston rod.

The central elements of the End-of-Content mechanism are;

The piston rod 10, disclosed in FIG. 7.
The piston rod guide 20, disclosed in FIG. 3.
The dose setting tube 30, disclosed in FIG. 6.
The EoC tube 40, disclosed in FIG. 4.
The driver 50, disclosed in FIG. 5.

These essential elements are also disclosed on the upper line view of FIG. 1 and again in FIG. 2.

The piston rod 10 which is also disclosed in FIG. 7 is externally provided with an outer thread 11 which is longitudinal interrupted by longitudinal tracks 12. The outer thread 11 is threaded to a similar inner thread provided in the nut member 15 secured in the housing 1 such that the piston rod 10 is moved helically forward in relation to the housing 1 when rotated relatively to the housing 1.

Figure 3:
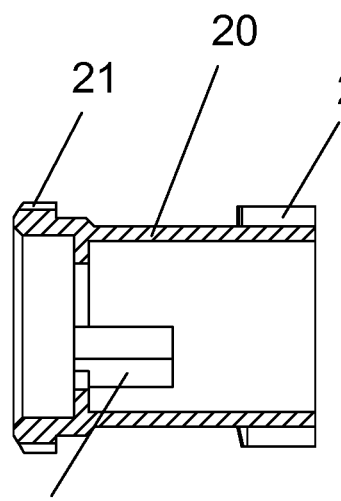
FIG. 3 show a side view of the piston rod guide.

The piston rod guide 20 depicted in FIG. 3 is on the outer surface distally provided with a one-way toothing 21 and proximally with a ring of radial teeth 22. On the inner surface, the piston rod guide 20 is provided with an inwardly pointing knob 23. The distal one-way toothing 21 rotationally secures the piston rod guide 20 relatively to the housing 1 such that the piston rod guide 20 can only rotate in one rotational direction. Further, the inwardly pointing knob 23 engages the longitudinal track 12 of the piston rod 10 such that the piston rod 10 is rotated whenever the piston rod guide 20 is rotated and vice versa.

The dose setting tube 30 disclosed in FIG. 6 is proximally coupled to the dose setting button 4 such that rotation of this dose setting knob 4 is transferred to a rotation of the dose setting tube 30. On the inner surface, the dose setting tube 30 is provided with an inwardly pointing thread segment 31, the meaning of which will be explained. Towards the distal end of the dose setting tube 30 an outwardly pointing peripheral ridge 32 is provided. This outwardly pointing peripheral ridge 32 couples the dose setting tube to the driver 50 as will be explained.

Figure 4:
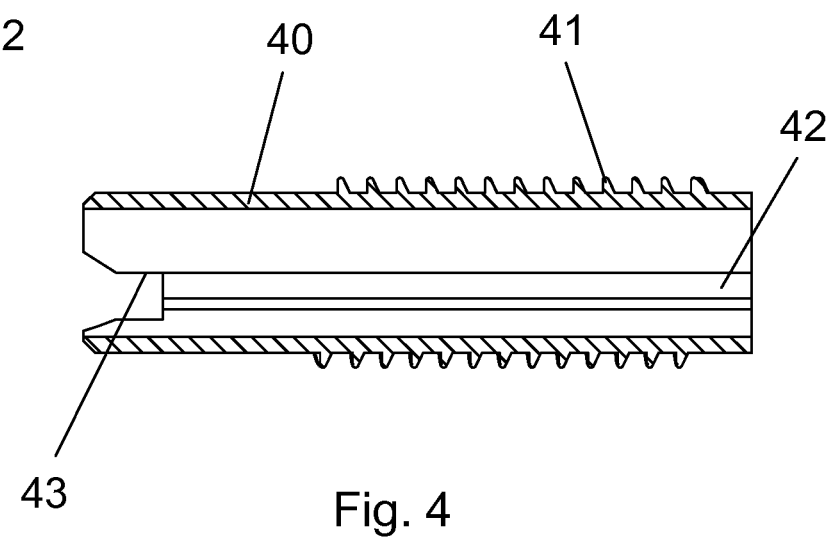
FIG. 4 show a side view of the EoC tube.

The End-of-Content tube 40 (here after the EoC tube 40) disclosed in FIG. 4 is externally provided with a thread 41 and internally with longitudinal ridges 42. The longitudinal ridges 42 slides in the longitudinal tracks 12 provided in the piston rod 10. The EoC tube 40 is henceforth not able to rotate relatively to the piston rod 10 but can noly slide axially in relation to the piston rod 10. Further, the distal end of the EoC tube 40 is provided with distal stop surfaces 43 and the proximal end is provided with proximal stop surfaces 44. The proximal stop surfaces 44 are provided at the termination of the thread 41 and can in one example be formed as an end surface of the thread 41.

The driver 50 is coupled to the dose setting tube 30 such that the driver 50 and the dose setting tube 30 both rotate in unison and move axially in unison. In one example the driver 50 and the dose setting tube 30 can be moulded as one constructive element. In a different example, the ridge 32 secures the dose setting tube 30 to the driver 50. The driver 50 is movable in the proximal direction during injection by the release element 9, which is moved proximally during injection. The proximal movement of the needle shield is thus translated to a proximal movement of the driver 50 and of the dose setting tube 30.

The driver 50 is distally provided with a plurality of inwardly pointing radial teeth 51 which are able to engage with the ring of radial teeth 22 provided on the outer surface of the piston rod guide 20.

The driver 50 is further connected to the torsion spring 5, which torsion spring 5 stores a torque which can be used to rotate the driver 50. The other end of the torsion spring is fixed relatively to the housing such that the torsion spring 5 is strained when the dose setting tube 30 and the driver 50 are rotated relatively to the housing 1 during dose setting. In the disclosed example the torsion spring 5 is fixated to a spring base 6 which is firmly fixed to the housing 1 to form a part of the housing structure.

The End-of-Content mechanism disclosed works as hereafter explained.

When a user wants to set a dose to be injected, the user rotates the dose setting tube 30 by operating the dose setting button 4. The dose setting button 4 connects to the dose setting tube 30 via the ratchet mechanism 7 and the dose setting tube 30 can move axially in relation to both the ratchet mechanism 7 and the dose setting button 4 during ejection as will be explained. This rotation of the dose setting tube 30 is instantly transferred to a rotation of the driver 50 and thus a straining of the torsion spring 5. The rotation of the dose setting tube 30 further forces the EoC tube 40 to move axially in the proximal direction as explained below.

During dose setting, as the dose setting tube 30 and the driver 50 is being rotated, the piston rod guide 20 is prevented form rotation in the dose setting direction by the one-way toothing 21 of the piston rod guide 20 engaging the housing 1. Since the piston rod guide 20 is prevented from rotation so is the piston rod 10 due to the engagement of the inwardly pointing knobs 23 on the piston rod guide 20 with the longitudinal tracks 12 of the piston rod 10. Since the piston rod 10 do not rotate, the EoC tube 40 does not rotate either since the longitudinal ridges 42 of the EoC tube 40 engages the longitudinal tracks 12 of the piston rod 10.

However, the rotation of the dose setting tube 30 and thereby of the inwardly pointing thread segment 31 forces the EoC tube 40 to move axially in the distal direction without rotating due to the interface between the thread segment 31 of the dose setting tube 30 and the outer thread 41 of the EoC tube 40. Once the thread segment 31 encounters the stop surface 44 of the thread 41, the dose setting tube 30 is prevented from further rotation and no further dose can be set by the user. In this End-of-Content position, the EoC tube 40 has been moved distally such that the distal stop surfaces 43 of the EoC tube 40 now engages with the inwardly pointing knob 23

During dose setting, the dose setting tube 30 and the driver 50 rotates whereas the piston rod 10, the piston rod guide 20, and the EoC tube 40 do not rotate but remain in their rotational positions. As a result the EoC tube 40 moves axially in the distal direction without rotating a distance which correlates to the size of the dose being set.

Whenever the user wants to perform an injection, the user presses the not-shown needle shield against the skin. The proximal movement of the needle shield is henceforth transferred to a proximal movement of the release element 9 and thereby of the driver 50.

As the driver 50 moves proximally the inwardly pointing radial teeth 51 of the driver 50 is moved into engagement with a ring of radial teeth 22 provided on the piston rod guide 20.

Since the dose setting tube 30 is coupled to the driver 50, the dose setting tube 30 follows the proximal movement of the driver 50 and moves out of engagement with the ratchet mechanism 7 and preferably also the dose setting button 4.

Once the dose setting tube 30 is moved proximally out of engagement with the ratchet mechanism 7, the torsion spring 5 is set free to rotate the driver 50 and preferably also the dose setting tube 30. As the driver 50 is rotated by the torsion spring 5, so is the piston rod guide 20 now engaged by the driver 50. As the piston rod guide 20 engages the longitudinal track 12 of the piston rod 10, the piston rod 10 rotates with the piston rod guide 20

During dose expelling the driver 50 and the dose setting tube 30 henceforth rotate and transforms the rotation to the piston rod guide 20 which thus also rotates. The rotation of the piston rod guide 20 further causes the piston rod 10 to rotate and since the longitudinal ridges 42 of the EoC tube 40 engages the longitudinal track 12 of the piston rod 10, the EoC tube 40 rotates together with the piston rod 10.

As the EoC tube 40 rotate together with the remaining elements, there is no relative movement of the EoC tube 40 and the position of the EoC tube 40 thus indicates the accumulated number of doses set and expelled as is common for an End-of-Content system.

Due to the engagement of the thread segment 31 on the dose setting tube 30 with the outer thread 41 of the EoC tube 40, the EoC tube 40 is also moved in the proximal direction during dose expelling.

Figure 8:
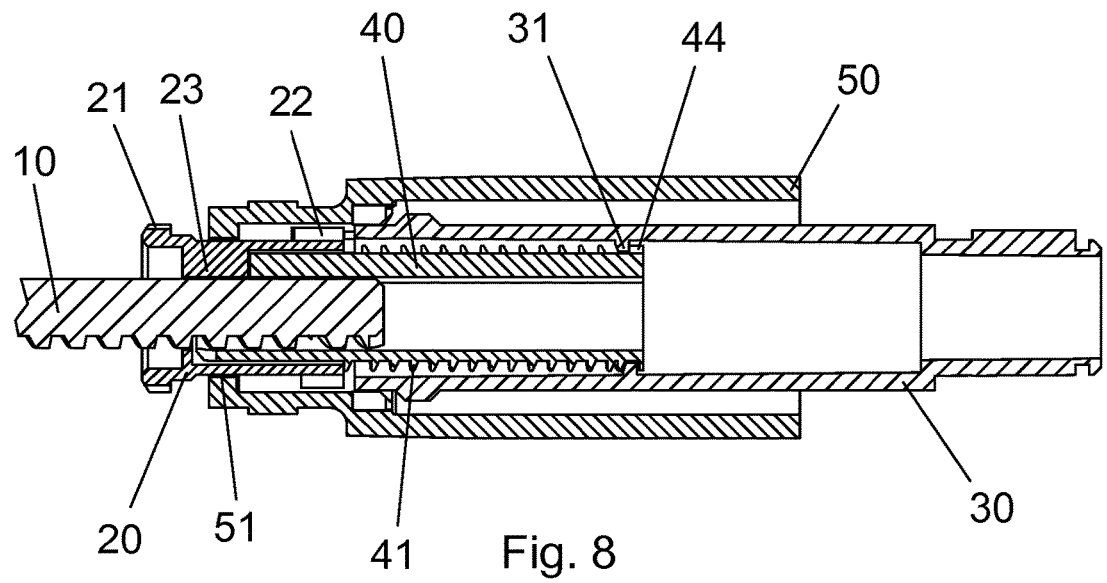
FIG. 8 a cross sectional view of the EoC mechanism during dose setting.

FIG. 8 discloses the EoC mechanism during dose setting. The driver 50 and the dose setting tube 30 are both in their distal position. In the example shown in FIG. 8, the End-of-Content position has been reached as the thread segment 31 abuts the stop surface 44. It is thus not possible to set a further dose since the distal stop surface 43 abut the inwardly pointing knob 23 and the proximal stop surface 44 abut the thread segment 31.

In this position and also in the positions where the distal stop surface 43 approaches the inwardly pointing knob 23, the EoC tube 40 and the piston rod guide 20 are rotationally locked to each other. This rotational locking can in some case make it difficult for the radial teeth 22 on the piston rod guide 20 to engage with the radial teeth 51 of the driver 50 if the teeth 22, 51 of the two engagement surfaces are not properly aligned.

Figure 9:
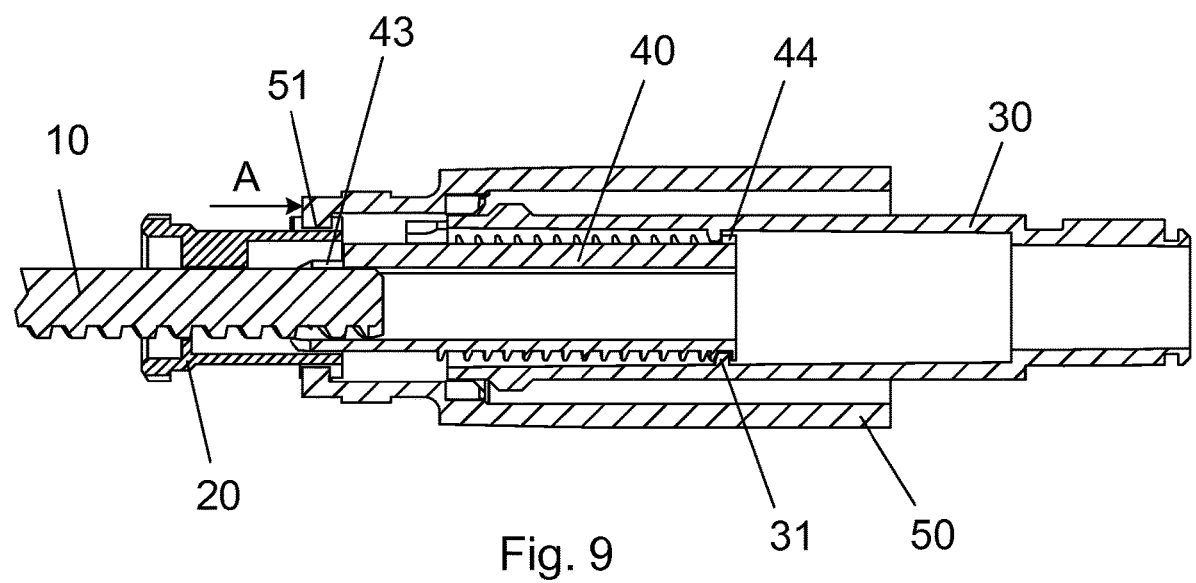
FIG. 9 a cross sectional view of the EoC mechanism during doging

FIG. 9 discloses the position during dose expelling. In this position, the driver 50 and the dose setting tube 30 has been moved proximally as indicated by the arrow "A". This is done by the activation of the not-shown needle shield and the release element 9. In this position the radial teeth 51 of the driver 50 have been moved into engagement with the radial teeth 22 on the piston rod guide 20. At the same time has the inwardly pointing thread segment 31 on the dose setting tube 30 lifted the EoC tube 30 a distance in proximal direction. This distance is set such that the distal stop surface 43 is lifted out engagement with the inwardly pointing knobs 23 on the piston rod guide 20. Due to this there is no longer rotational connection between the piston rod guide 20 and the EoC tube 40 during dose expelling and the piston rod guide 20 is thus free to rotate a few degrees which makes it possible for the piston rod guide 20 to enter into engagement with the radial teeth 51 of the driver 50 should the piston rod guide 20 and the driver 50 not be fully aligned.

Some preferred embodiments have been shown in the foregoing, but it should be stressed that the invention is not limited to these, but may be embodied in other ways within the subject matter defined in the following claims.

The invention claimed is:

1. An injection device for apportioning set doses of a liquid drug from a reservoir comprising:
    a housing,
    a rotatable piston rod for driving out the set doses from the reservoir, having an outer thread and a longitudinal non-threaded area,
    a piston rod guide rotatable during dose expelling only and engaging the longitudinal non-threaded area of the piston rod to rotate the piston rod during dose expelling,
    a rotatable drive element for rotating the piston rod guide during dose expelling wherein the drive element is axially movable between a first dose setting position and a second dose expelling position,
       wherein the drive element in the first dose setting position is disengaged from the piston rod guide and in the second dose expelling position engages with the piston rod guide,
    a torsion spring encompassed between the housing and the drive element for rotating the drive element during dose expelling,
    an End-of-Content (EoC) tube having an inwardly pointing ridge engaging the non-threaded area of the piston rod, to thereby rotate with the piston rod during dose expelling, and further provided with an outer thread,
    a rotatable dose setting tube coupled to the drive element and provided with a thread segment threadely engaging the outer thread of the EoC tube,
    wherein during dose setting rotation of the dose setting tube and the drive element relatively to the piston rod which does not rotate during dose setting causes the EoC tube to move distally an axial distance in relation to the dose setting tube due to the threaded engagement between the rotatable dose setting tube 30 and the EoC tube engaging the piston rod; the axial distance correlating to the size of the set dose and the EoC tube being able to move distally until a proximal stop surface provided on the EoC tube engages the thread segment on the dose setting tube thereby preventing further distal movement of the EoC tube and further rotation of the rotatable dose setting tube,
    and wherein during dose expelling the dose setting tube, the drive element, the piston rod guide and the EoC tube rotate together maintaining the EoC tube in its relative position in relation to the dose setting tube.

2. The injection device according to claim 1, wherein the drive element and the dose setting tube is moved proximally from the first dose setting position to the second dose expelling position by a release element.

3. The injection device according to claim 2, wherein the release element is structured to be activated by an axially movable needle shield and wherein the proximal movement of the drive element and the dose setting tube causes the EoC tube to also move proximally.

4. The injection device according to claim 1, wherein the thread segment is provided on an inner surface of the dose setting tube.

5. The injection device according to claim 1, wherein the piston rod guide is provided with an inwardly pointing knob engaging the longitudinal non-threaded area of the piston rod.

6. The injection device according to claim 1, wherein the EoC tube distally is provided with a distal stop surface.

7. The injection device according to claim 6, wherein the distal stop surface on the EoC tube engages the inwardly pointing knob on the piston rod guide when the thread segment engages the proximal stop surface provided on the EoC tube.

8. The injection device according to claim 1, wherein the proximal stop surface provided on the EoC tube forms part of the thread.

9. The injection device according to claim 1, wherein the piston rod guide is provided with a one-way toothing engaging the housing.

10. The injection device according to claim 1, wherein the piston rod guide is provided with radial teeth for engaging the drive member during dose expelling.

11. The injection device according to claim 1, wherein the outer thread on the piston rod engages a similar corresponding inner thread provided in the housing or in a nut member secured in the housing.

* * * * *